United States Patent
Lee et al.

(10) Patent No.: US 7,031,750 B2
(45) Date of Patent: Apr. 18, 2006

(54) MANAGEMENT METHOD OF FAT MASS AND MANAGEMENT DEVICE OF FAT MASS USING MOBILE PHONE

(75) Inventors: Min-Hwa Lee, Seoul (KR); Moon-Soo Kim, Seoul (KR)

(73) Assignee: HealthPia America, Co. Ltd, Palisades, NJ (US)

( * ) Notice: Subject to any disclaimer, the term of this patent is extended or adjusted under 35 U.S.C. 154(b) by 0 days.

(21) Appl. No.: 10/479,685

(22) PCT Filed: Jul. 2, 2003

(86) PCT No.: PCT/KR03/01297

§ 371 (c)(1),
(2), (4) Date: Jun. 7, 2004

(87) PCT Pub. No.: WO2004/006160

PCT Pub. Date: Jan. 15, 2004

(65) Prior Publication Data

US 2004/0220491 A1 Nov. 4, 2004

(30) Foreign Application Priority Data

Jul. 2, 2002 (KR) .................. 10-2002-0037908

(51) Int. Cl.
*A61B 5/05* (2006.01)
*A61N 1/08* (2006.01)
*G06F 17/60* (2006.01)
*H04M 1/00* (2006.01)

(52) U.S. Cl. .................. 455/556.1; 607/72; 607/547; 705/2

(58) Field of Classification Search ............ 455/426.1, 455/3.05, 420, 556.1; 702/30; 600/509, 600/547; 607/5, 72; 705/2
See application file for complete search history.

(56) References Cited

U.S. PATENT DOCUMENTS

| 4,008,712 | A | * | 2/1977 | Nyboer | 600/547 |
| 4,895,163 | A | * | 1/1990 | Libke et al. | 600/547 |
| 4,947,862 | A | * | 8/1990 | Kelly | 600/547 |

(Continued)

FOREIGN PATENT DOCUMENTS

JP 02000126331 A * 5/2000

*Primary Examiner*—William Trost
*Assistant Examiner*—Kiet Doan
(74) *Attorney, Agent, or Firm*—Jenkens & Gilchrist

(57) ABSTRACT

The present invention relates generally to an apparatus for managing the body fat of a human body and, more particularly, to a mobile communication terminal in which a body fat managing function is embedded, and an apparatus in which a body fat managing device is connected to a mobile communication terminal. The mobile communication terminal, in which a body fat managing function is embedded, includes a signal amplifying and converting unit for converting the measured value of body fat, a low frequency generating unit for generating low frequency waves, an input unit for receiving the body fat-related items, a display unit for displaying the measured value of the body fat, a memory unit for storing the measured value of the body fat, an adaptor unit connected to outside electrode lines, and a control unit for controlling the respective function units. Additionally, a body fat managing device, which is used while being connected to a mobile communication terminal, includes a signal amplifying and converting unit, a low frequency generating unit, an electrode unit and a conduction unit.

3 Claims, 4 Drawing Sheets

U.S. PATENT DOCUMENTS

| | | | |
|---|---|---|---|
| 5,372,141 A * | 12/1994 | Gallup et al. | 600/547 |
| 5,792,063 A * | 8/1998 | Danielsson et al. | 600/509 |
| 6,088,615 A * | 7/2000 | Masuo | 600/547 |
| 6,654,631 B1 * | 11/2003 | Sahai | 600/509 |
| 2001/0004732 A1 * | 6/2001 | Satoh | 705/2 |
| 2002/0052697 A1 * | 5/2002 | Serita | 702/30 |
| 2002/0087093 A1 * | 7/2002 | Chai | 600/547 |
| 2002/0138117 A1 * | 9/2002 | Son | 607/72 |
| 2003/0055460 A1 * | 3/2003 | Owen et al. | 607/5 |

* cited by examiner

MANAGEMENT METHOD OF FAT MASS AND MANAGEMENT DEVICE OF FAT MASS USING MOBILE PHONE

TECHNICAL FIELD

The present invention relates generally to an apparatus for managing the body fat of a human body and, more particularly, to a mobile communication terminal in which a body fat managing function is embedded, and an apparatus in which a body fat managing device is connected to a mobile communication terminal.

BACKGROUND ART

Fatness in which body fat exceeds a normal value may be a cause of various adult diseases, such as cerebral apoplexy and myocardial infarction. In order to manage such body fat, people in modem times frequently measure the body fat, and use a variety of therapies, such as acupuncture, to remove the body fat.

Reference numeral 100 of FIG. 1 designates a conventional body fat measuring apparatus. As depicted in this drawing, when an examinee attaches electrodes 111, 112, 113 and 114 to the right arm and right foot of a human body and inputs the age, weight and height of the examinee using a keyboard 130, a body composition measuring unit analyzes body composition and, thereafter, outputs result values through a display 110 and a printer 120.

Reference numeral 150 of FIG. 1 designates a conventional body fat removing apparatus. The principle of the body fat removing apparatus is to obtain an effect of resolving body fat by sending a low frequency current to certain regions, such as a neck and an abdomen, through two + and − pads 151 and 152. The examinee can set the intensity and duration of a low frequency current through the keyboard 170 and confirm them on the display 160.

However, as shown in FIG. 1, the prior art scheme is inconvenient in that an examinee who desires to manage body fat should carry the respective apparatuses. An examinee desires to measure/remove body fat anytime and anywhere he likes, but it is unreasonable in practice to carry the body fat measuring apparatus and the body fat removing apparatus each having an input unit and a display unit. Accordingly, an apparatus for integrally performing body fat management, including body fat measurement and removal, has been demanded.

DISCLOSURE OF THE INVENTION

Accordingly, the present invention has been made keeping in mind the above problems occurring in the prior art, and an object of the present invention is to facilitate the carrying of a body fat managing apparatus by enabling body fat to be measured and removed through a mobile communication terminal that becomes a necessity of people in modem times, and allowing input and output functions required for body fat management to be performed by the input and display units of the mobile communication terminal. Another object of the present invention is to efficiently manage body fat by allowing the measured value of the body fat to be transmitted to and stored in the memory unit of a mobile communication terminal, or a body fat management server via a wireless network, and downloading a prescription for managing the body fat.

In order to accomplish the above object, the present invention proposes a mobile communication terminal in which a mobile communication terminal in which a body fat managing function is embedded, and an apparatus in which a body fat managing device is connected to a mobile communication terminal.

A mobile communication terminal, in which a body fat managing function is embedded, includes a signal amplifying and converting unit for amplifying and converting impedance measured by electrode pads attached to a certain region of a human body, a low frequency generating unit for generating low frequency signals, a display unit for displaying body fat-related items including the measured value of the body fat, a memory unit for storing the measured value, an input unit for receiving the body fat-related items, a wireless unit for wireless transmission, an adaptor unit connected to lines connected to the outside electrode pads, and a control unit for controlling the respective function units.

A body fat managing device, which is used while being connected to a mobile communication terminal, includes a signal amplifying and converting unit used to measure body fat, an electrode unit and electrode pads for outputting a voltage and a current, a low frequency generating unit used to remove the body fat, and a conduction unit for conducting low frequency waves to a human body.

When body fat is measured using the mobile communication terminal in which a body fat managing function is embedded, or the apparatus in which the mobile communication terminal is connected to the body fat managing device, the mobile communication terminal automatically stores the measured value of the body fat in the memory, or a certain server via the wireless network. The measured value of the body fat is automatically stored without the manipulation of an examinee, so that it is possible to systematically manage the body fat.

BEST MODE FOR CARRYING OUT THE INVENTION

Hereinafter, embodiments of the present invention will be described in detail with reference to the accompanying drawings.

Figure 1:
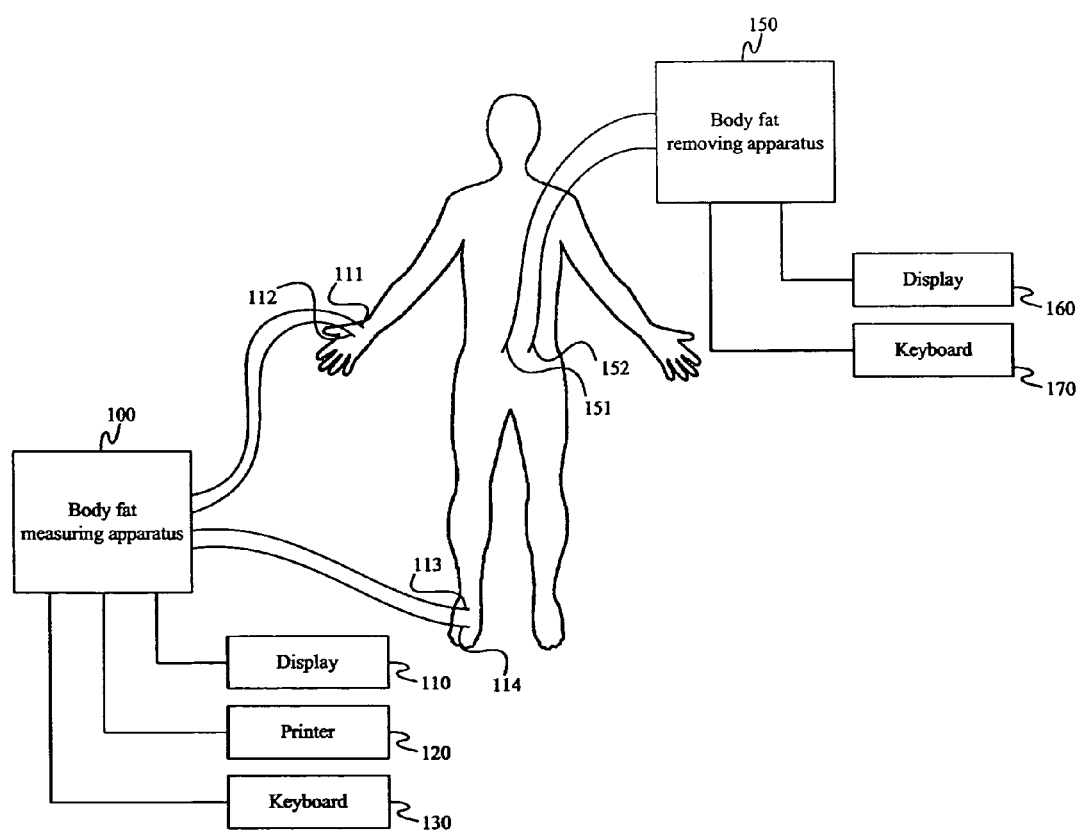
FIG. 1 is a diagram showing the use of conventional body fat measuring apparatus and body fat removing apparatus.
Figure 2:
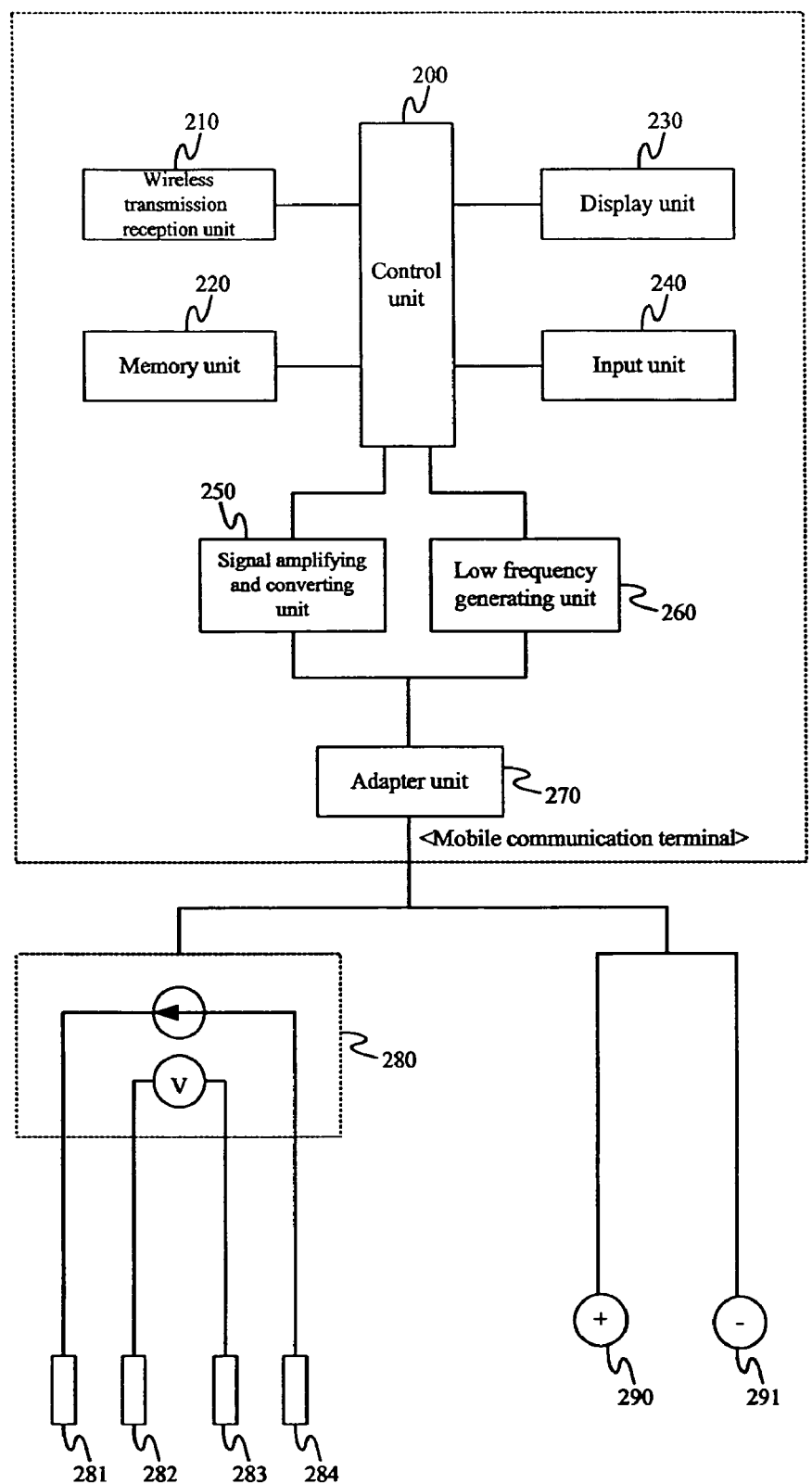
FIG. 2 is a block diagram of a mobile communication terminal in which a body fat managing function is embedded in accordance with the present invention.

FIG. 2 is a block diagram of a mobile communication terminal in which a body fat managing function is embedded in accordance with the present invention.

A user normally uses the mobile communication terminal in a wireless communication mode, and then the user selects a body fat measurement or removal mode through an input unit 240 when the user desires to measure or remove body fat.

First, the operation of the mobile communication terminal in the body fat measurement mode will be described.

The input unit 240 receives the height, age, gender and weight of an examinee from the examinee prior to the measurement of body fat. The height, age and etc. are used in the measurement of body fat of the examinee. That is, Total Body Water (TBW), body fat (FAT) and a body fat rate (%FAT) are calculated from impedance measured through an electrode unit 280 and the weight, age, weight and gender input through the input unit 240, and these calculated values are displayed on a display unit 230. The impedance is obtained through first to fourth electrodes 281, 282, 283 and 284. While a sine wave Alternating Current (AC) is applied to a closed circuit formed by one of the first and second electrodes 281 and 282 and one of the third and fourth electrodes 283 and 284 connected to the former electrode through the human body, the impedance can be obtained by measuring a voltage value between the other of the first and second electrodes 281 and 282 and the other of the third and fourth electrodes 283 and 284 connected to the former electrode through the human body. The impedance is amplified and converted to a digital signal by a signal amplifying and converting unit, and the digital signal is transferred to a control unit 200. The control unit 200 calculates body fat from the impedance and the bodily information input from the examinee. The measured value of the body fat is stored in a memory unit 220 or is transmitted to the body fat managing server through a wireless transmission and reception unit, so that the details of the body fat is stored and managed.

Since the impedance measuring method and the body fat calculating method are the same as those of the conventional body fat measuring apparatus, a detailed description of them is omitted here.

Meanwhile, when the user selects a body fat removal mode through the input unit 240, a low frequency generating unit 260 generates low frequency pulses in a frequency band of 10 to 120 Hz and transfers them to a conduction unit 290 and 291 so as to resolve and remove body fat accumulated in the human body. The conduction unit 290 and 291 is provided with a plurality of surface contact pads to conduct low frequency pulses, generated in the low frequency generating unit 260, to a fat region of the user while being in contact with the fat region.

The control unit 200 functions to control respective function units. An adapter unit 270 is a connecting part where measurement/removal conduction lines are connected to the mobile communication terminal.

Figure 3:
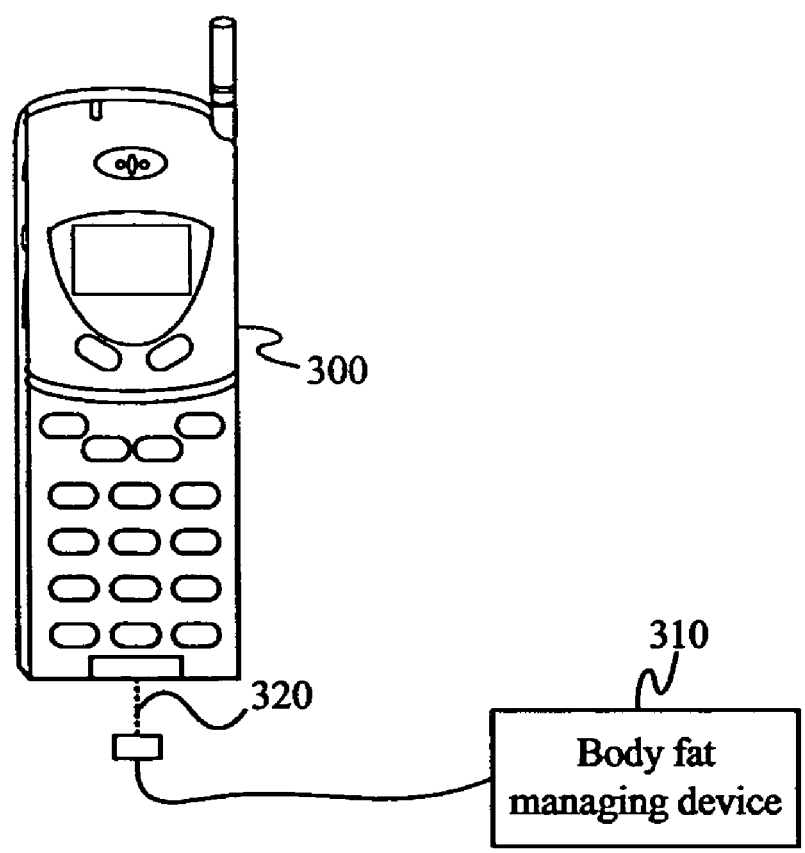
FIG. 3 is a diagram showing a body fat managing device connected to a mobile communication terminal.

FIG. 3 is a diagram showing a body fat managing device connected to a mobile communication terminal.

In the past, a conventional body fat measuring apparatus and a conventional body fat removing apparatus should be separately provided, but the body fat managing device 310 of the present invention implements both a body fat measuring function and a body fat removing function. Additionally, the body fat managing device 310 does not need a display and a keyboard that are required by each of the conventional body fat measuring and removing apparatuses. That is, the body fat managing device 310 performs only body fat measuring and removing functions, and the input and display of information are performed by the mobile communication terminal 300. An existing mobile communication terminal may be used as the mobile communication terminal of the present invention through the installation of a body fat management program. The installation of the body fat management program is accomplished by downloading the fat managing program from a communication company via wireless communication, or downloading the body fat management program from a body fat managing server while accessing the Internet.

The body fat managing device 310 includes first to fourth electrode pads. After the examinee sets the operation mode of the mobile communication terminal to the body fat measurement mode so as to measure impedance, and thereafter inputs bodily information, such as height, weight, etc. through the input unit of the mobile communication terminal. Thereafter, the mobile communication terminal 300 calculates body fat using the impedance measured by the body fat managing device 310 and the bodily information of the examinee input through the input unit, and displayed the calculated body fat of the examinee on the display unit of the mobile communication terminal.

Furthermore, the body fat managing device 310 is provided with a low frequency generating unit and electrode pads for removing body fat, thus being capable of removing body fat. The user selects the body fat removal mode through the input unit of the mobile communication terminal, and thereafter sets driving time, etc.

The body fat managing device 310 is connected to the serial port of the mobile communication terminal 300 via a cable or the like and exchanges necessary information, such as the measured values of body fat, with the mobile communication terminal.

Figure 4:
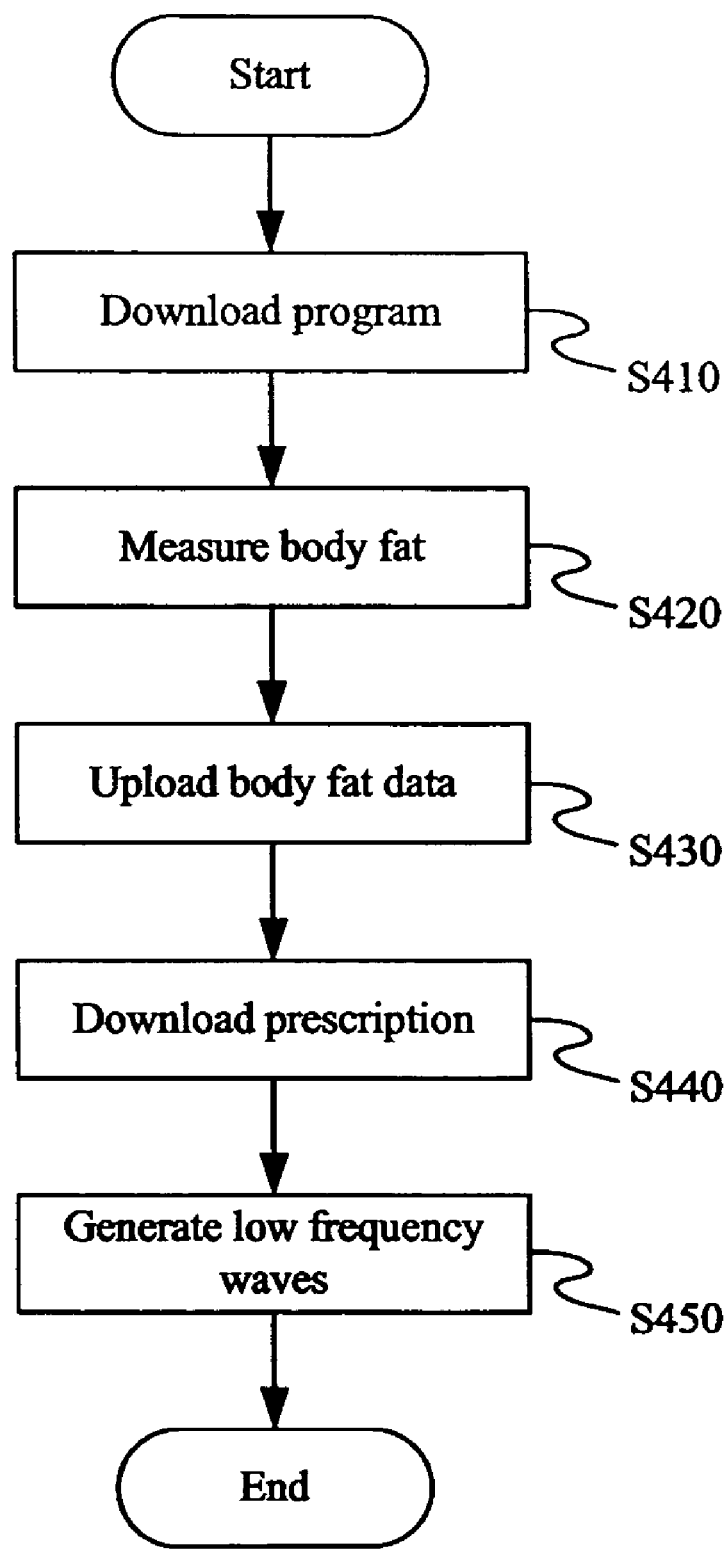
FIG. 4 is a flowchart showing a method of managing body fat using the mobile communication terminal.

FIG. 4 is a flowchart showing a method of managing body fat using the mobile communication terminal.

The mobile communication terminal manages body fat using the body fat management program. Accordingly, the mobile communication terminal downloads the body fat management program from a certain server on the Internet via a wireless network at step S410. Thereafter, body fat is measured using the mobile communication terminal in which the body fat managing function is embedded or the body fat managing device of FIG. 3 at step S420. The data of the measured body fat is uploaded to the body fat managing server on the Internet, by use of the mobile communication terminal via the wireless network at step S430. Thereafter, the mobile communication terminal receives a prescription corresponding to the measured body fat from the server at step 440. The contents of the prescription include the magnitude of low frequency waves, the generating time of the low frequency waves and the range of the low frequency waves. Additionally, the amount of excise and a menu proper for a day may be reported to the examinee.

When the examinee requests the removal of body fat, the mobile communication terminal activates a low frequency generating unit to generate low frequency waves of a proper magnitude according to the received prescription at step S450. Additionally, the received amount of excise and menu are displayed on the display unit of the mobile communication terminal to allow the examinee to view them, thus allowing the examinee to efficiently manage body fat.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described above, the present invention adds both a body fat measuring function and a body fat removing function to a mobile communication terminal, so that a user can conveniently manage body fat at any time while carrying only the mobile communication terminal. Additionally, since an input unit and a display unit, which are used to measure and remove body fat, can be implemented in the mobile communication terminal, the present invention is advantageous from an economic point of view.

The invention claimed is:

1. A mobile communication terminal in which a body fat managing function is embedded, comprising:
   an input unit for receiving an input to switch the mobile communication terminal between a communication mode, a body fat measurement mode and a body fat removal mode;
   a display unit for displaying a measured value of the body fat;
   a memory unit for storing the measured value of the body fat after the body fat has been measured;
   a wireless unit for transmitting the measured value of the body fat to a body fat measuring server on a wireless network after the body fat has been measured;
   an adaptor unit for connecting an electrode line for measuring the body fat and a low frequency transmission line for removing the body fat to the mobile communication terminal;
   a signal amplifying and converting unit for amplifying measured impedance and converting the amplified impedance into a digital signal in the body fat measurement mode;
   a low frequency generating unit for generating low frequency signals in the body fat removal mode; and
   a control unit for controlling the function units and calculating the measured value of the body fat from the measured impedance.

2. An apparatus for managing body fat, comprising:
   a body fat managing device including an electrode unit for measuring bodily impedance of an examinee, a signal amplifying and converting unit for amplifying the impedance measured by the electrode unit and converting the amplified impedance into a digital signal, a low frequency generating unit for generating low frequency signals, and a conduction unit provided with electrode pads for conducting low frequency waves to a body of an examinee; and
   a mobile communication terminal equipped with the body fat measuring device, the mobile communication terminal including an input unit for receiving bodily information of the examinee and for switching the mobile communication terminal between a communication mode, a body fat measurement mode and a body fat removal mode, a display unit for displaying a measured value of the body fat, a memory unit for storing the measured value of the body fat, a wireless unit for transmitting the measured value of the body fat to a body fat measuring server on a wireless network, an adaptor unit connected to the body fat managing device, and a control unit for controlling the units and calculating the measured value of the body fat from the measured impedance.

3. A method of managing body fat using a mobile communication terminal, comprising the steps of:
   downloading a body fat management program onto the mobile communication terminal from a body fat managing server on an Internet;
   switching the mobile communication terminal from a communication mode to a body fat measurement mode;
   measuring body fat of an examinee;
   uploading data of the body fat from the mobile communication terminal to the body fat managing server;
   downloading a prescription for management of the body fat from the body fat managing server to the mobile communication terminal;
   switching the mobile communication terminal from a communication mode to a body fat removal mode; and
   generating low frequency waves according to the prescription.

* * * * *